US008900268B2

(12) United States Patent
Weidenhagen et al.

(10) Patent No.: US 8,900,268 B2
(45) Date of Patent: Dec. 2, 2014

(54) ENDOSCOPIC WOUND CARE TREATMENT SYSTEM AND METHOD

(76) Inventors: Rolf Weidenhagen, Munich (DE);
Klaus Uwe Grützner, Gauting (DE)

( * ) Notice: Subject to any disclaimer, the term of this patent is extended or adjusted under 35 U.S.C. 154(b) by 1037 days.

(21) Appl. No.: 10/289,867

(22) Filed: Nov. 7, 2002

(65) Prior Publication Data

US 2004/0093026 A1 May 13, 2004

(51) Int. Cl.
*A61D 1/00* (2006.01)

(52) U.S. Cl.
USPC ............. 606/215; 606/213; 604/2; 604/131; 604/289; 604/304; 604/305; 604/313; 604/319; 604/352; 128/897

(58) Field of Classification Search
USPC .......... 606/215, 153, 213; 604/304, 289, 305, 604/313, 319, 352, 535, 540, 543, 290, 604/164.01–164.11; 128/897; 600/574
See application file for complete search history.

(56) References Cited

U.S. PATENT DOCUMENTS

| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,969,057 A | 1/1961 | Simmons |
| 3,367,332 A | 2/1968 | Groves |
| 3,520,300 A * | 7/1970 | Flower, Jr. .................... 604/269 |
| 3,648,692 A | 3/1972 | Wheeler |
| 3,682,180 A | 8/1972 | McFarlane |
| 3,826,254 A | 7/1974 | Mellor |
| 3,908,664 A | 9/1975 | Loseff |
| 4,080,970 A | 3/1978 | Miller |
| 4,096,853 A | 6/1978 | Weigand |
| 4,139,004 A | 2/1979 | Gonzalez |
| 4,165,748 A | 8/1979 | Johnson |
| 4,233,969 A | 11/1980 | Lock et al. |

(Continued)

FOREIGN PATENT DOCUMENTS

| AU | 550575 A1 | 8/1982 |
| AU | 745271 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.

(Continued)

*Primary Examiner* — Vy Q Bui
(74) *Attorney, Agent, or Firm* — RatnerPrestia

(57) ABSTRACT

An endoluminal and intracorporeal negative pressure, wound care treatment, and prophylaxic system 10 and method includes a pressure distributor 40 for placement substantially within an internal organ or tissue abscess 34. A fluidic communication means 22 is provided between the pressure distributor 40 and a negative pressure source 20. A collection canister 24 is provided between the negative pressure source 20 and the pressure distributor 40 for collecting any effluents 36 that may be drawn from the abscess 34 during application of negative pressure. An introducing conduit 44 is provided for introducing the pressure distributor 40 into the abscess 34. A positioning conduit 46 is provided to properly position the pressure distributor 40 within the abscess 34. Negative pressure is applied to the pressure distributor 40 in order to provide negative pressure therapy within the abscess 34.

30 Claims, 3 Drawing Sheets

(56) References Cited

U.S. PATENT DOCUMENTS

| | | | |
|---|---|---|---|
| 4,245,630 A | 1/1981 | Lloyd et al. | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman et al. | |
| 4,392,853 A | 7/1983 | Muto | |
| 4,392,858 A | 7/1983 | George et al. | |
| 4,419,097 A | 12/1983 | Rowland | |
| 4,475,909 A | 10/1984 | Eisenberg | |
| 4,480,638 A | 11/1984 | Schmid | |
| 4,525,166 A * | 6/1985 | Leclerc | 604/133 |
| 4,525,374 A | 6/1985 | Vailancourt | |
| 4,533,352 A * | 8/1985 | Van Beek et al. | 604/317 |
| 4,540,412 A | 9/1985 | Van Overloop | |
| 4,543,100 A | 9/1985 | Brodsky | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,324,306 A * | 6/1994 | Makower et al. | 606/213 |
| 5,344,415 A | 9/1994 | Debusk et al. | |
| 5,358,494 A | 10/1994 | Svedman | |
| 5,374,261 A * | 12/1994 | Yoon | 604/385.01 |
| 5,380,290 A * | 1/1995 | Makower et al. | 604/164.01 |
| 5,437,622 A | 8/1995 | Carion | |
| 5,437,651 A * | 8/1995 | Todd et al. | 604/313 |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,836,311 A * | 11/1998 | Borst et al. | 128/897 |
| 5,853,421 A * | 12/1998 | Leschinsky et al. | 606/213 |
| 5,921,972 A | 7/1999 | Skow | |
| 6,015,378 A * | 1/2000 | Borst et al. | 600/37 |
| 6,071,267 A | 6/2000 | Zamierowski | |
| 6,142,982 A | 7/2000 | Hunt et al. | |
| 6,135,116 A | 10/2000 | Vogel et al. | |
| 6,235,009 B1 * | 5/2001 | Skow | 604/317 |
| 6,345,623 B1 | 2/2002 | Heaton et al. | |
| 6,458,109 B1 * | 10/2002 | Henley et al. | 604/304 |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,004,915 B2 | 2/2006 | Boynton et al. | |
| 7,198,046 B1 | 4/2007 | Argenta et al. | |
| 7,338,482 B2 * | 3/2008 | Lockwood et al. | 604/543 |
| 7,799,004 B2 * | 9/2010 | Tumey | 604/313 |
| 2001/0029956 A1 | 10/2001 | Argenta et al. | |
| 2002/0115951 A1 | 8/2002 | Norstream et al. | |
| 2002/0120185 A1 | 8/2002 | Johnson | |
| 2002/0143286 A1 | 10/2002 | Tumey | |
| 2004/0030304 A1 | 2/2004 | Hunt et al. | |

FOREIGN PATENT DOCUMENTS

| | | |
|---|---|---|
| AU | 755496 | 12/2002 |
| CA | 2005436 | 6/1990 |
| EP | 0117632 A2 | 1/1984 |
| EP | 0100148 | 2/1984 |
| EP | 0161865 | 11/1985 |
| EP | 0358 302 | 3/1990 |
| EP | 1 018 967 B1 | 8/2004 |
| GB | 692578 | 6/1953 |
| GB | 2 197 789 A | 6/1988 |
| GB | 2333965 A | 8/1999 |
| GB | 2329127 B | 8/2000 |
| SG | 71559 | 4/2002 |
| WO | WO 80/02182 | 10/1980 |
| WO | WO 93/09727 | 5/1993 |
| WO | WO/94/20041 | 9/1994 |
| WO | WO 96 05873 A1 | 2/1996 |
| WO | WO 97/18007 | 5/1997 |
| WO | WO 99/13793 | 3/1999 |

OTHER PUBLICATIONS

Susan Mendez-Eastman, RN; When Wounds Won't Heal, RN Jan. 1998, vol. 61(1); Medical Economics Company, Inc., Montvale, NJ, USA.

James H. Blackburn, II, MD. et al; Negative-Pressure Dressings as a Bolster for Skin Grafts; Annals of Plastic Surgery, vol. 40, No. 5, May 1998, pp. 453-457.

John Masters; Letter to the editor; British Journal of Plastic Surgery, 1998, vol. 51(3), p. 267; Elsevier Science/The British Association of Plastic Surgeons, UK.

S.E. Greer, et al; The Use of Subatmospheric Pressure Dressing Therapy to Clos Lymphocutaneous Fistulas of the Groin; British Journal of Plastic Surgery (2000), 53.

George V. Letsou, M.D., et al; Stimulation of Adenylate Cyclase Activity in Cultured Endothelial Cells Subjected to Cyclic Stretch; Journal of Cardiovascular Surgery, 31, 1990.

PCT International Search Report; PCT international application PCT/GB98/02713; Jun. 8, 1999.

PCT Written Opinion; PCT international application PCT/GB98/02713; Jun. 8, 1999.

PCT International Examination and Search Report, PCT international application PCT/GB96/02802; Jan. 15, 1998 and Apr. 29, 1997.

PCT Written Opinion, PCT international application PCT/GB/96/02802; Sep. 3, 1997.

Kostyuchenok, B.M, et al. ;Vacuum Treatment in the Surgical Management of Purulent Wounds; Vestnik Khirurgi, Sep. 1986.

Davydov, Yu. A., et al; Vacuum Therapy in the Treatment of Purulent Lactation Mastitis; Vestnik Khirurgi, Sep. 1986.

Yusupov, Yu. N., et al; Active Wound Drainage, Vestnik Khirurgi, vol. 138, Issue 4, 1987.

Davydov, Yu. A., et al; Bacteriological and Cytological Assessment of Vacuum Therapy of Purulent Wounds; Vestnik Khirurgi, Oct. 1988.

Davydov, Yu. A., et al; Concepts for the Clinical-Biological Management of the Wound Process in the Treatment of Purulent Wounds by

(56) References Cited

OTHER PUBLICATIONS

Means of Vacuum Therapy; Vestnik Khirurgi.

International Search Report for PCT international application PCT/GB95/01983; Nov. 23, 1995.

Patent Abstract of Japan; JP4129536; Terumo Corporation; Apr. 30, 1992.

Orringer, Jay, et al., "Management of Wounds in Patients with Complex Enterocutaneous Fistulas", Surgery, Gynecology & Obstertics, Jul. 1987, V. 165, pp. 79-80.

* cited by examiner

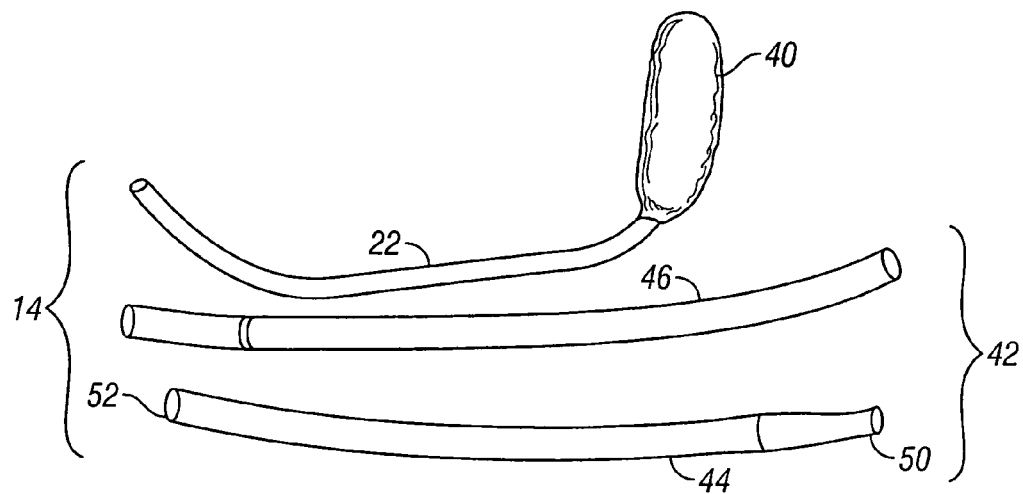
FIG. 2
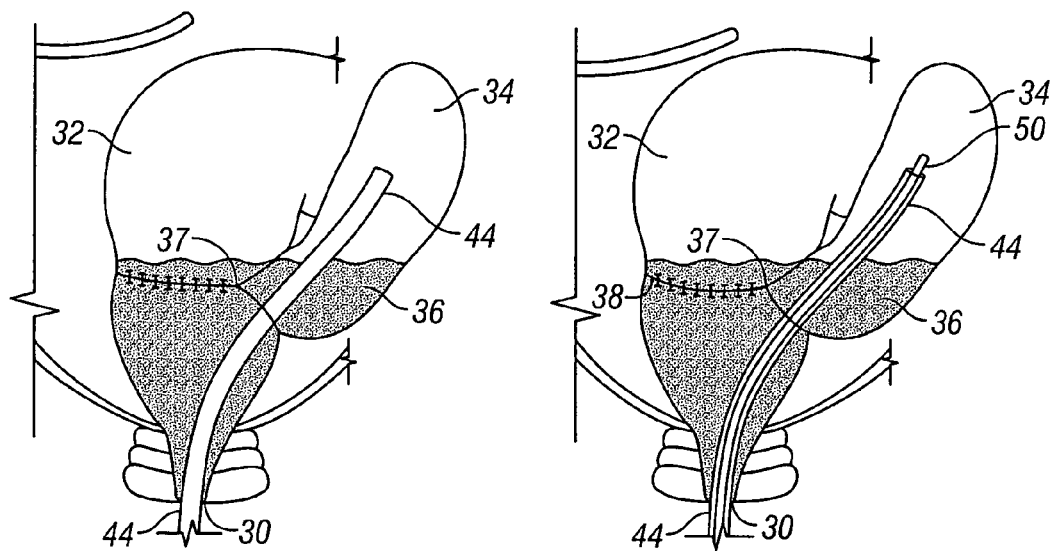
FIG. 3A          FIG. 3B

ENDOSCOPIC WOUND CARE TREATMENT SYSTEM AND METHOD

FILED OF THE INVENTION

This invention relates to endoscopic wound care treatment, and in particular the treatment of perianastomotic abscesses. More specifically this invention relates to an endoluminal and intracorporeal negative pressure abscess, wound care, and prophylaxic treatment system and method.

BACKGROUND OF THE INVENTION

Negative pressure therapy has been utilized for the healing of open wounds and has been commercialized by Kinetic Concepts, Inc. of San Antonio, Tex., by its proprietary V.A.C.® product line. In practice, the application to a wound of negative gauge pressure, typically involves the mechanical-like contraction of the wound with simultaneous removal of excess fluid. In this manner, V.A.C.® therapy augments the body's natural inflammatory process while alleviating many of the known intrinsic side effects, such as the production of edema caused by increased blood flow absent the necessary vascular structure for proper venous return. As a result, V.A.C.® therapy has been highly successful in the promotion of wound closure, healing many wounds previously thought largely untreatable. However, treatment utilizing V.A.C.® therapy has been largely limited to open surface wounds. Treatment of internal wounds, such as internal abscesses, has typically involved more traditional techniques. Other more complicated internal conditions, such as anastomotic leakage has been even more problematic to treat.

There are a host of intraabdominal sites in which abscesses may occur. In certain endoscopic procedures, such as anterior resection of the rectum, complications may occur leading to anastomotic leakage, which in turn may lead to an abscess formation. Some studies have shown that anastomotic leakage after anterior resection of the rectum occurs anywhere from 4.5% to 18% of the time. Such problems are often aggravated by a physiologic obstruction in the anal region. Accumulation of gases and feces results in movement of this waste material through the path of least resistance, which in most cases, and especially in the case of anastomotic leakage, is out of the colonic lumen and into the abdominal cavity. The backflow into the abdominal cavity leads to a pressure build up next to the anastomosis, which in turn leads to mechanical enlargement of the tissue at the anastomosis and formation of an abscess. Proper healing of the anastomosis is therefore continually impaired.

Little has been known about the best way to treat such anastomotic leakage. Some standard procedures include nasogastric suction, broad-spectrum antibiotics, and parenteral nutrition. Other surgical procedures have included drainage of the leakage, loop colostomy, resection of the anastomosis (known as the Hartmann's procedure to those skilled in the art), and abdominoperineal excision of the rectum with a terminal stoma.

These procedures can be very invasive and costly. Additionally, the physical and emotional trauma to the patient can be quite extensive, especially in cases necessitating excision of the rectum.

For the foregoing reasons, there is a need for an endoscopic wound care treatment system that is capable of treating an internal organ or tissue abscess in a minimally invasive manner.

It is therefore an object of the present invention to provide an endoscopic wound care treatment system having an endoscopic component, that provides a means for introducing the endoscopic component, which is preferably a negative pressure distributor, into an internal organ or tissue, and in particular into an internal wound or abscess of a human body.

A further object is to provide such a system that is capable of achieving a closed abscess in a shorter period of time than current methods allow, with less trauma to the patient than current methods.

SUMMARY

In accordance with the foregoing objects, the present invention generally comprises a collecting means, which is preferably a pressure distributor for placement substantially within an internal organ, cavity, or tissue abscess. A fluidic communication means is provided between the pressure distributor and a negative pressure source for communicating gases, liquids, and possible solid waste matter such as necrotic tissue and/or feces from the organ or tissue abscess. A collection canister is provided between the negative pressure source and the pressure distributor for collecting any effluents that may be drawn from the abscess or internal organ during application of negative pressure. An introducing conduit is provided for introducing the pressure distributor into the abscess or cavity. A positioning conduit is provided to properly position the pressure distributor within the abscess or cavity. Negative pressure is applied to the pressure distributor in order to provide negative pressure therapy within the abscess or cavity.

The present invention includes a collecting means having fluid channels, which also serves as a pressure distributor and that may be comprised of an open-cell, polyurethane foam having a pore size in the range of about 400 to 600 microns. The foam may be cut to a size corresponding to the geometry of an anastomotic leakage and its corresponding cavity, which may range from 7.0 cm in length and 3.0 cm in diameter to 0.5 cm×1.0 cm. The invention further comprises a system for placing the foam within the cavity. An evacuation tube comprises at least one port that communicates with the foam and is positioned at the distal end of the tube or on a side proximate to the distal end of the tube. The distal end of the evacuation tube is preferably placed in the middle of the foam. The foam may be fixed to the tube using a non-absorbable surgical suture. Alternatively, the foam may be welded or glued to the tube using techniques known to those skilled in the art. Other alternative embodiments include the use of biodegradable foam, in which case the foam is fixed to the evacuation tube using biodegradable means, such as bioabsorbable sutures. The opposing, or proximal, end of the tube is connected to a high-vacuum drainage system, into which effluent fluid may be collected. A subatmospheric pressure of up to 850 mbar is applied to the foam. The open-cell nature of the foam ensures equal distribution of the applied pressure to every surface of the cavity in contact with the foam, thus serving as a pressure distributor.

The present invention also includes an introducer for placing and positioning the foam within the abscess or cavity. The introducer comprises at least one tubular element. The tubular element of the introducer may be the lumen of an endoscope. Preferably, the tubular element is a flexible silicone sleeve, although it is to be understood that a rigid tube may also be utilized. More preferably the introducer consists of two coaxially arranged silicone sleeves. The inner diameter of the outer sleeve is larger than the outer diameter of a standard endoscope that may be used in the present invention. Preferably, the inner diameter is about 1.0 mm larger than the outer diameter of an endoscope. The outer sleeve is used as the introducer sleeve for introducing the foam into the cavity. The lumen of the inner sleeve is larger than the diameter of the evacuation tube and is used as a positioner for the foam dressing. Preferably, the lumen of the inner sleeve is 2.0 mm larger than the outer diameter of the evacuation tube. The introducer sleeve has a smaller outer diameter than the inner diameter of the outer sleeve. The foam is pushed forward to the end of the introducer sleeve, by the inner sleeve, with the evacuation tube in its inner channel. In certain instances, the introducer sleeve may not be necessary, such as might occur when the evacuation tube provides sufficient rigidity to push the foam out of the outer sleeve. The foam in its compressed state is positioned inside the outer sleeve and expands to its usual size after being released from the outer sleeve.

Upon placement of the foam within the cavity, the introducer may be removed, and negative pressure applied to the foam. Application of negative pressure, which is evenly distributed by the foam, allows for an immediate reduction in size of the abscess or cavity, effective removal of effluents from the wound or abscess, and eventual healing or significant improvement of the wound or abscess through minimally invasive and cost effective means.

It is to be understood that the system of the present invention may be used in prophylactic or therapeutic applications. Since it is known in the art that a number of surgical procedures on the human body result in post-operative complications, in particular wound healing disorders like abscess formations and anastomotic dehiscence, the system of the present invention may advantageously be employed for avoiding and/or treating such post-operative complications. For example, the surgeon may apply the endoscopic component to the wound prior to closing the incision. Care needs to be taken that the fluidic communication means is positioned such that undesired effluents, such as pus, are conveniently removed from the body. Advantageously, the endoscopic component is positioned such that the undesired fluid is removed via a natural body orifice and/or surgical incision. To ensure adequate drainage of body fluids from cavities or intraluminal tracts such as the gastrointestinal tract, no negative pressure or a low negative pressure may be applied.

Alternatively, the system of the invention may be used in the treatment of complications or diseases arising from operations or, for example, from infections by bacterial or other pathogenic microorganisms. In accordance with the invention it is envisaged that anastomotic leakage, preferably of the esophagus, stomach, small or large intestine, pancreatic duct, or the tracheal or bronchial system is treated. Additionally, fistulas such as entero-enteric fistulas (such as Crohn's disease) entero-cutaneous fistulas or recto-vaginal fistulas may be treated. A further option in accordance with the invention is the treatment of spontaneous or post-operative organ abscesses (e.g. from the spleen or pancreas). Abscesses of body compartments may also be treated, such as thoracic abscesses (e.g. thoracic empyema, postpneumonia, tuberculotic abscesses) as well as abscesses resulting from inflictions such as shotgun wounds or wounds arising from knives and the like. Also within the scope of the invention are treatments following vascular prosthesis infections.

In principle, the system of the invention may be applied in a variety of different ways. The system of the present invention may be applied under direct visualization (by hand or using surgical instruments). Endoscopic, coloscopic, laparoscopic, thoracoscopic, and radiologic applications are also possible. The invention may also be utilized in conjunction with open surgery.

The invention also relates to a method of prophylaxis or treatment of a disease related to abscess formation inside the human or animal body comprising inserting the endoscopic wound care treatment system of the present invention into the human body and locating the endoscopic component to the site of abscess formation or expected abscess formation. Preferably, the endoscopic component is introduced via a body orifice into the human or animal body. Alternatively, it may be introduced at the site of an incision performed during a surgical procedure on a human or animal. The method of the invention is similarly applicable to the preferred embodiments described herein.

The method of the invention may be used both in actual treatment processes as well as prophylactically to inhibit or slow down abscess formation, for example, as a result of an operation performed on a human or animal body.

The foregoing has outlined some of the more pertinent objects of the present invention. These objects should be construed to be merely illustrative of some of the more prominent features and applications of the invention. Many other beneficial results can be attained by applying the disclosed invention in a different manner or by modifying the invention as will be described. Accordingly, other objects and a fuller understanding of the invention may be had by referring to the following Detailed Description of the Invention, which includes the preferred embodiment

BRIEF DESCRIPTION OF THE DRAWINGS

These and other features and advantages of the invention will now be described with reference to the drawings of certain preferred embodiments, which are intended to illustrate and not to limit the invention, and wherein like reference numbers refer to like components, and in which:

FIG. 2 is a perspective view of the primary components of the endoscopic portion, which includes the introducer, of a system that operates in accordance with the present invention.

FIGS. 3A-3E are perspective cross-sectional views of the endoscopic portion of a system that operates in accordance with the present invention in the treatment of a perianastomic abscess of the rectum.

DETAILED DESCRIPTION

Figure 1:
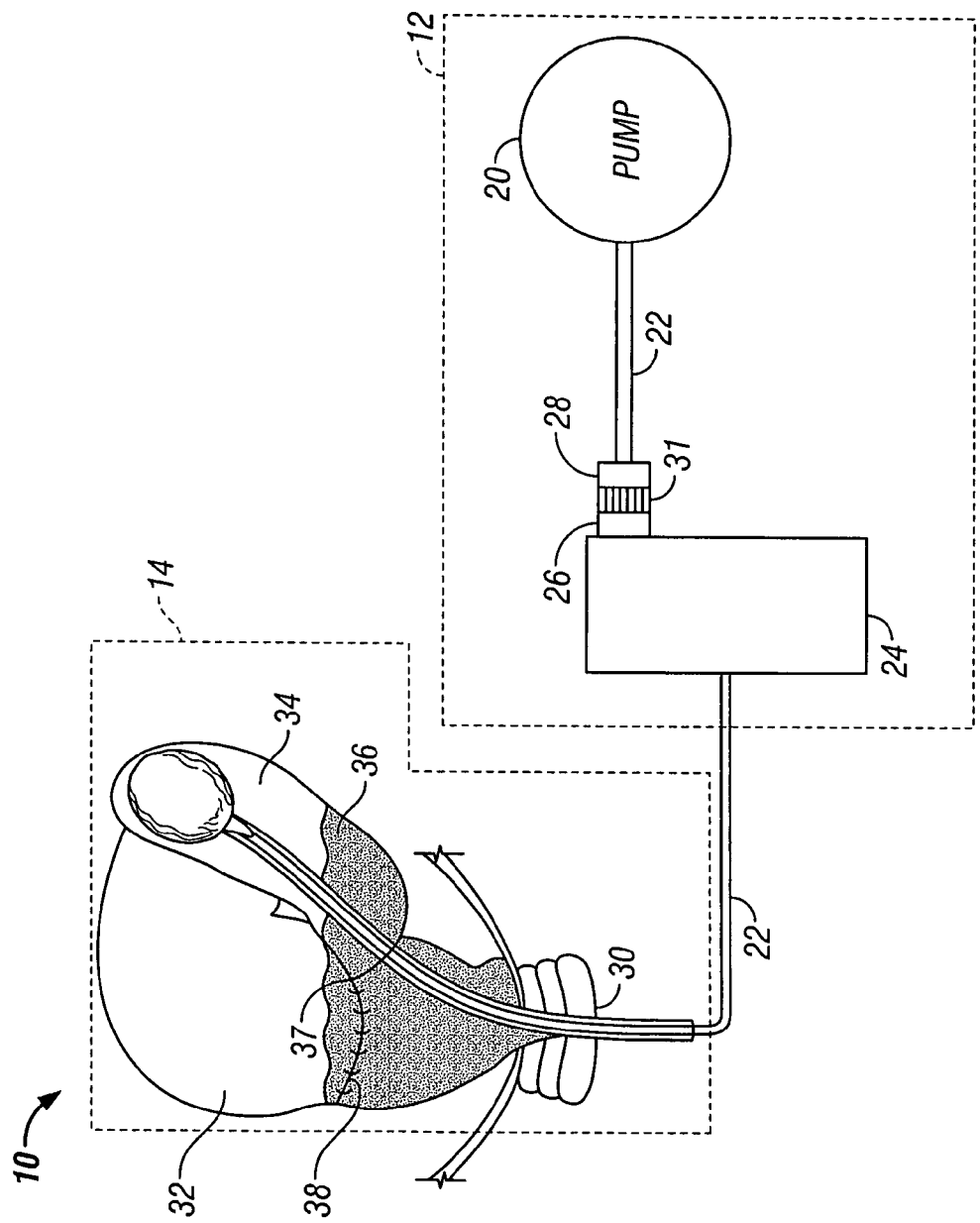
FIG. 1 is a block diagram illustrating the primary components of a system that operates in accordance with the present invention.

Although those of ordinary skill in the art will readily recognize many alternative embodiments, especially in light of the illustrations provided herein, this detailed description is exemplary of the preferred embodiment of the present invention as well as alternate embodiments, the scope of which is limited only by the claims that may be drawn hereto.

Furthermore, while the term "endoscopic" is often used in medical terminology to describe the visualization of the interior of organs and cavities of an human or animal body utilizing an endoscope, it is to be understood that the term "endoscopic," and its grammatical derivatives, as used herein is intended to encompass and also include laparoscopic, thoracoscopic, radiologically guided or direct open application (e.g. open surgery), general surgery, and prophylaxis. More specifically, the term "endoscopic" as used herein refers generally to endoluminal and intracorporeal negative-pressure abscess, wound care, and prophylaxic treatment systems and modalities, and is not intended to be limited to the traditional medical definition of the term.

The details of the preferred embodiments of the present invention are graphically and schematically illustrated in the accompanying drawings. Like elements in the drawings are represented by like numbers, and any similar elements are represented by like numbers with a different lower case letter suffix.

Referring now to FIG. 1 in particular, there is illustrated the primary components of an endoscopic wound care treatment system 10 that operates in accordance with the present invention. The treatment system 10 is further divided into a vacuum component 12 and an endoscopic component 14.

The vacuum component 12 includes a negative pressure source 20, fluid communication means 22, and a collection canister 24. The negative pressure source 20 is preferably a portable electronic pump, so as to allow for increased mobility of the patient during application of negative pressure to the wound or abscess. It is to be understood however, that other means of supplying negative pressure are contemplated. Such negative pressure supply means may include, but are not limited to stationary sub-atmospheric sources, such as may be found in hospital rooms having wall suction ports connected to a centralized sub-atmospheric pressure source. Other alternative negative pressure sources may include hand pumps. Alternatively, effluents may be removed by gravity force.

While several alternative negative pressure sources may be utilized, including the ones mentioned, it is to be understood that the present invention is most effective when applying an initial pressure of up to about 850 mbar. (0.84 atm). Thereafter, it is anticipated that a negative pressure anywhere in the range of about 10-1003 mbar (0.01-0.099 atm) may be utilized to maintain application of negative pressure within the abscess, either continuously or intermittently. A more preferable pressure range of about 101-1003 mbar (0.1-0.99 atm) of negative pressure may also be utilized. Most preferably, a pressure range of about 507-861 mbar (0.5-0.85 atm) of negative pressure is utilized.

The negative pressure component 12 also includes a collection canister 24 in removable fluidic communication with the negative pressure source 20. The collection canister 24 is utilized to collect any effluents that may be drawn from the wound or abscess during application of negative pressure. The collection canister 24 is intended to be removable from negative pressure component 12 so as to be disposed of when full and replaced with a clean and empty canister, without having to dispose of the entire negative pressure component 12. It is anticipated that a canister having a capacity of about 200-300 mL is most preferable, although various sizes of canisters are available and may be utilized. The size of the canister 24 to be used may be determined by the amount of effluents that may be drawn and the preference of the caregiver or patient. A first hydrophobic membrane filter 26 may be interposed between the canister 24 and the negative pressure source 20, in order to prevent effluents, that may be drawn from the wound or abscess cavity, from contaminating the negative pressure source 20. The first filter 26 may also serve as a fill-sensor for the canister 24. As effluents contact the first filter 26, a signal is sent to the negative pressure source 20, causing it to shut down.

According to an alternative embodiment of the present invention, a second hydrophobic filter 28 may be interposed between the first filter 26 and the negative pressure source 20. The addition of the second filter 28 is advantageous when the first filter 26 is also used as a fill sensor for the canister 24. In such a situation, the first filter 26 may act as a fill sensor, while the second filter 28 further inhibits contamination of effluents into the negative pressure source 20. This separation of functions into a safety device and a control (or limiting) device, allows for each device to be independently engineered.

An odor vapor filter 31, which may be a charcoal filter, may be interposed between the first filter 26 and the second filter 28, in order to counteract the production of malodorous vapors that may be present in the effluents or the abscess, and which are being drawn by the negative pressure source 20. A further embodiment allows for first 26 and second filters 28 to be incorporated as an integral part of the canister 20 to ensure that the filters 26, 28, at least one of which are likely to become contaminated during normal use, are automatically disposed of in order to reduce the exposure of the system to any contaminants that may be trapped by the filters 26, 28.

The vacuum component 12 also includes a fluid communication means 22, which is preferably composed of a flexible and biocompatible tubing material, well known to those of ordinary skill in the relevant art. Exemplary tubing material includes the preferred embodiment of a flexible silicone tubing, although it is to be understood that a rigid tubing may also be utilized. In the preferred embodiment the tube includes a port having a diameter in the range of about 500-2000 microns. It is to be understood that the port sizes having a diameter in the range of 100-5000 microns may also be utilized, and that although the preferred shape of the port is circular, oblong or rectangular shapes of similar sizes may be alternatively utilized. The fluid communication means 22 communicates between, and is incorporated into, the vacuum component 12 and the endoscopic component 14. The endoscopic component 14 is insertable into an orifice 30 or opening either naturally occurring in the human body or through surgical intervention, such as the anus of a patient or surgical incision (which also includes radiological intervention). The endoscopic component 14 passes through the internal organ or cavity 32, such as the rectum or colon of the patient, and into the abscess 34 that has formed, which may also contain effluents 36 or other waste material such as necrotic tissue, debris, or feces. The abscess 34 commonly forms along an opening 37 of an anastomosis 38, or similar sutured incision, or similarly weakened portion of an internal organ or body cavity, such as may occur after anterior resection of the rectum.

Turning now to FIG. 2, the fluid communication means 22 is fixedly connected to the pressure distributor 40 of the endoscopic component 14, which serves as a collecting means. The fluid communication means 22 may be fixedly connected to the pressure distributor 40, using a non-absorbable surgical suture, welding, or similar means known to those of ordinary skill in the art. Alternatively, the fluid communication means 22 and pressure distributor 40 may be integrally formed, especially when both are made of the same material. In a further embodiment, the pressure distributor 40 may be comprised of a bioabsorbable material, in which case, the pressure distributor 40 is connected to the fluid communication means 22 by bioabsorbable or biodegradable means, such as bioabsorbable sutures. In such an embodiment the pressure distributor 40 remains within the body and is not removed after treatment.

In the preferred embodiment the pressure distributor 40 is an open-cell, polyurethane ether foam, commonly used in conjunction with V.A.C.® therapy to treat open wounds. The open-cell nature of the foam comprises pores, which preferably have a diameter in the size range of about 400-600 microns. The foam may be cut according to the size and geometry of the abscess 34 to be treated. It is anticipated that the size range of foams required is likely in the range of about 7.0 cm in length and 3.0 cm in diameter to about 0.5 cm×1.0 cm. It is also contemplated that foams of varying sizes may be prefabricated in numerous size ranges within the size ranges specified, so as to eliminate, or reduce the need for a caregiver to cut the foam. Larger or smaller foams may also be utilized, depending on the geometry of the wound or abscess to be treated. Additionally, it is envisioned that more than one foam may be placed within a treatment site.

Alternative embodiments of the present invention may also include foams that are coated with wound treatment substances, such as antibiotics or antiviral agents. Further alternative embodiments include the introduction of local anesthetics prior to removal of the pressure distributor 40 from the patient, so as to improve and manage pain that may be associated with the procedure. In such an instance, approximately 5-10 ml of local anesthetic is introduced into the pressure distributor through the fluid communication means 22, by means of a syringe or active pumping mechanism known in the art. In further alternative embodiments, other fluids, such as a high-pressure saline lavage, or antimicrobial agents, may be actively administered to the pressure distributor 40 through the fluid communication means 22.

During application of negative pressure to the pressure distributor 40 by the negative pressure source 20, the open-cell nature of the foam ensures substantially equal distribution of the pressure to every surface of the cavity in contact with the foam. It is to be understood that while the preferred embodiment utilizes an open-cell foam for use as the pressure distributor 40, other materials may also be utilized that exhibit the necessary and equivalent features, such as malleability and porosity exhibited by the preferred embodiment described herein.

The endoscopic component 14 also includes an introducer 42 for introducing and positioning the pressure distributor 40 within the abscess 34. The introducer 42 is comprised of an outer sleeve 44 and an inner sleeve 46, which are preferably single lumen, flexible tubes, which may be made of silicone or a similar material. In use, the outer sleeve 44 is coaxially arranged about the inner sleeve 46, as illustrated in FIG. 3D.

Returning now to FIG. 2, the lumen of the outer sleeve 44 is about 1.0 mm larger than the outer diameter of the distal end of a standard endoscope known to those of ordinary skill in the art. A typical endoscope has a diameter in the range of about 0.5 cm to about 1.5 cm. Therefore, the outer sleeve 44 preferably has an opening lumen diameter in the range of about 0.6 cm to about 1.6 cm. The lumen of the inner sleeve 46 is about 2 mm larger than the diameter of the fluid communication means 22 and is used as a positioner for the pressure distributor 40. A typical fluid communication means 22 is a standard evacuation tube with side ports (not shown) within the pressure distributor, which may be made of silicone, or a similar material. An exemplary evacuation tube of the type used as the fluid communication means 22 in the preferred embodiment is an Ulmer drain from Maersk Medical of Denmark.

The outer sleeve 44 is used as the introducer sleeve for introducing the pressure distributor into the cavity 34. The outer sleeve 44 may have a distal end 50 that is of a slightly smaller or tapered diameter than the rest of the outer sleeve 44 for ease of insertion into the orifice 30 of the patient. The lumen of the inner sleeve is 2 mm larger than the diameter of the fluid communication means 22 and is used as a positioner for the pressure distributor 40.

Figure 3E:
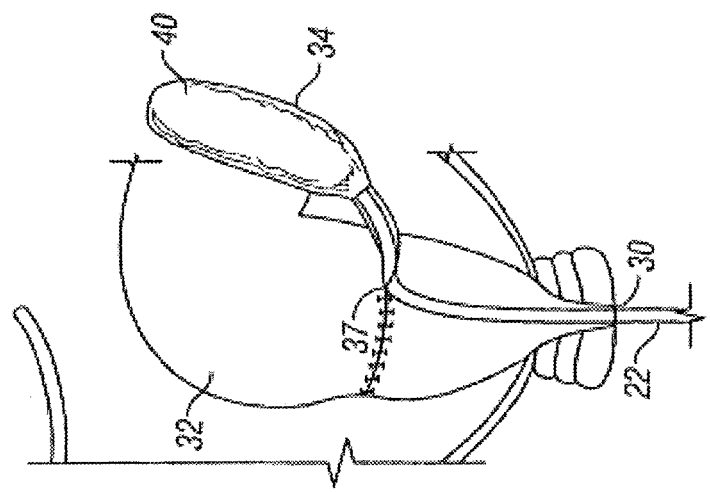
Figure 3D:
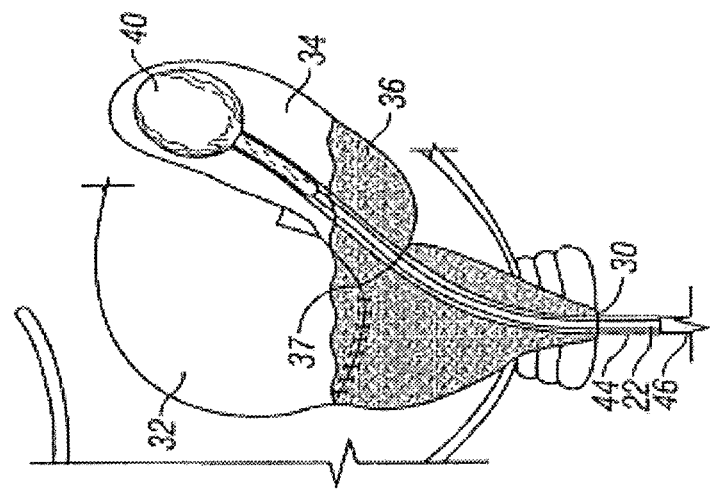
Figure 3C:
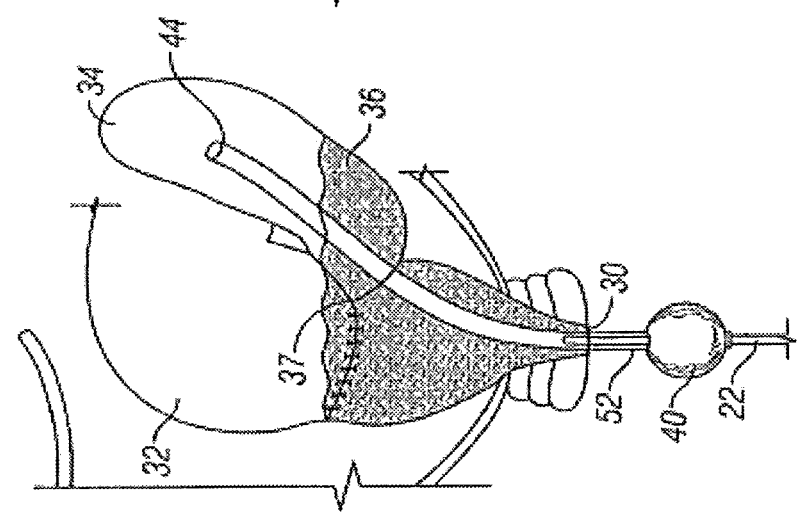

Turning now to FIGS. 3A-3E, there is illustrated the means in which the introducer 42 is utilized in accordance with the present invention. As shown in FIG. 3A, the outer sleeve 44 is positioned within the abscess 34 after having been passed through the orifice 30, the internal cavity 32, and the opening 37 of the anastomosis 38. The distal end 50 of the outer sleeve 44 is tapered to allow for easier passage through orifice 30 and opening 37 in the anastomosis 38, as illustrated in FIG. 3B. Alternatively, the outer sleeve 44 may be positioned about a standard endoscope (not shown) such that the distal end 50 of the outer sleeve is at the same level as the distal end (not shown) of the endoscope (not shown). The outer sleeve 44 is positioned by endoscopic guidance into the cavity using the endoscope. The endoscope can thereafter be removed and the outer sleeve 44 kept in place.

The inner sleeve 46 is positioned about the fluid communication means 22, and approximate the pressure distributor 40. The pressure distributor 40 is pushed forward through the proximal end 52 of the outer sleeve 44 and through the distal end 50 of the outer sleeve, by the inner sleeve 46, as is illustrated in FIGS. 4C and 4B. The malleable and porous nature of the pressure distributor 40 allows it to be compressed as it passes through the outer sleeve 44, and return to its original size and configuration. The inner sleeve 46 is used to position the pressure distributor 40 within the abscess 34.

After the pressure distributor 40 is adequately positioned within the abscess 34, both the introducer 42, consisting of the outer sleeve 44 and the inner sleeve 46 is removed, leaving the pressure distributor 40 in place within the abscess 34. Preferably the inner sleeve 46 is removed first and then the outer sleeve 44 is removed. Negative pressure, supplied by the negative pressure source 20 is communicated through the fluid communication means 22, resulting in application of negative pressure within the abscess 34, which in turn results in reduction in size, as shown in FIG. 3E. In order to provide adequate negative pressure, airtight sealing of the pressure distributor may be necessary. This may be accomplished by the geometry of the cavity or lumen being treated by the pressure distributor. Similarly, an airtight seal may be achieved by the anatomy of the place and path along which the endoscopic component 14 is inserted into the body. For example, airtight sealing by the anus of the patient after insertion of the endoscopic component 14 into a paraanastomotic abscess cavity after rectal surgery. Alternatively, an airtight seal can be accomplished by the use of an adhesive drape known to those skilled in the art of vacuum assisted wound closure of wounds on the body surface. Eventual healing of the abscess may therefore be accomplished.

The introducer 42 may be reintroduced into the abscess 34 in order to remove the pressure distributor 40 after completion of treatment. Alternatively, the introducer 42 may be left in place in order to facilitate removal and reapplication of the pressure distributor 40 within the abscess 34. It is also possible to remove the pressure distributor 40 by pulling the fluid communication means 22 out of the patient. The connection of the pressure distributor 40 and the fluid communication means 22 of the endoscopic component 14 should be of sufficient strength that the endoscopic component 14 can be removed as one unit. Similarly, the strength of the connection should be sufficient to overcome any adhesion between the pressure distributor 40 and any granulation tissue that may have grown into the pores during application of negative pressure. It is preferred that the tensile strength of the connection between the pressure distributor 40 and the fluid communication means 22, as well as the tensile strength of the communication means 22 itself, is capable of withstanding a force of at least about 60 Newtons.

While the invention has been described herein with reference to certain preferred embodiments, theses embodiments have been presented by way of example only, and not to limit the scope of the invention. Many other variations are possible, which would be obvious to one skilled in the art. Accordingly, the scope of the invention should be identified only in accordance with the claims that follow.

We claim:

1. An endoscopic wound care treatment system for treatment of an internal cavity of a patient, comprising:

a vacuum component providing a negative pressure source disposed on a proximal end of a fluid communication means, the fluid communication means in the form of a tube;

an endoscopic component in fluid communication with the vacuum component, the endoscopic component including:

a fluid collecting means, said collecting means being fixedly connected to said fluid communication means, and said collecting means being adapted to collect and guide fluid to the fluid communication means;

an introducer including an outer sleeve and an inner sleeve, the introducer being adapted for introducing and positioning the collecting means within an internal organ, cavity or tissue abscess, wherein the outer sleeve of the introducer is configured to introduce the collecting means within the internal organ, cavity, or tissue abscess and the inner sleeve of the introducer is disposed within the outer sleeve and is configured to position the collecting means within the internal organ, cavity, or tissue abscess and the inner sleeve having a lumen larger than the diameter of the fluid communication means; and the collecting means being disposed on a distal end of said fluid communication means, said collecting means having an outer surface defining a three-dimensional structure, the collecting means uncovered over the outer surface and configured such that negative pressure produced by the vacuum component is evenly distributed over the outer surface.

2. The endoscopic wound care treatment system of claim 1 wherein said vacuum component is comprised of a collection canister in fluidic communication with said negative pressure source.

3. The endoscopic wound care treatment system of claim 2 further comprising a first hydrophobic filter in fluidic communication with said collection canister.

4. The endoscopic wound care treatment system of claim 3 further comprising a second hydrophobic filter in fluidic communication with said first hydrophobic filter.

5. The endoscopic wound care treatment system of claim 4, wherein a vapor filter is interposed between the first hydrophobic filter and the second hydrophobic filter.

6. The endoscopic wound care treatment system of claim 3, wherein the first hydrophobic filter is a fill sensor.

7. The endoscopic wound care treatment system of claim 1 wherein said collecting means is comprised of an open-cell foam.

8. The endoscopic wound care treatment system of claim 1 wherein said fluid communication means is integrally formed with said collecting means.

9. The endoscopic wound care treatment system of claim 1 wherein said outer sleeve is further comprised of a tapered distal end.

10. The endoscopic wound care treatment system of claim 1, wherein said inner sleeve is in coaxial arrangement with said outer sleeve.

11. The endoscopic wound care treatment system of claim 10 wherein said outer sleeve is about 0.6 cm to about 1.6 cm.

12. The endoscopic wound care treatment system of claim 11 wherein said inner sleeve is coaxially and removably arranged about said fluid communication means.

13. The endoscopic wound care treatment system of claim 12 wherein said inner sleeve is about 2 mm larger than an outer diameter of said fluid communication means.

14. The endoscopic wound care treatment system of claim 1, wherein the vacuum component is a stationary sub-atmospheric source.

15. An endoscopic wound care component, comprising:

a fluid collecting means and a fluid communication means in the form of a tube, wherein said collecting means is fixedly connected to said fluid communication means, and said collecting means is adapted to collect and guide fluid to the fluid communication means; and an introducer including an outer sleeve and an inner sleeve, the introducer being adapted for introducing and positioning the collecting means within an internal organ, cavity or tissue abscess, wherein the outer sleeve of the introducer is configured to introduce the collecting means within the internal organ, cavity, or tissue abscess and the inner sleeve of the introducer is disposed within the outer sleeve and is configured to position the collecting means within the internal organ, cavity, or tissue abscess and the inner sleeve having a lumen larger than the diameter of the fluid communication means; and wherein a proximal end of said fluid communication means opposite to a distal end is operably connected to a vacuum component to provide a negative pressure source.

16. The endoscopic component of claim 15 wherein said collecting means comprises an elastically compressible structure having fluid channels.

17. The endoscopic component of claim 15 wherein said collecting means comprises an open-cell polyurethane foam.

18. The endoscopic component of claim 17 wherein said open-cell polyurethane foam has a pore size in the range of 400 to 600 microns.

19. The endoscopic component of claim 15 wherein said collecting means is adapted to act as a negative pressure distributor.

20. The endoscopic component of claim 15 wherein said fluid communication means comprises a tube having a distal end, further comprising at least one port being provided proximate said distal end.

21. The endoscopic component of claim 20 wherein said port has a diameter in the range of 100 to 5000 microns.

22. The endoscopic component of claim 15 wherein said fluid communication means comprises a flexible structure having a tensile strength of at least about 60 Newtons.

23. The endoscopic component of claim 15 further comprising fixation means for connecting said collecting means to said fluid communication means.

24. The endoscopic component of claim 23 wherein said collecting means comprises a proximal end and a distal end and wherein at least said proximal end of the collecting means is fixed to said fluid communication means.

25. The endoscopic component of claim 24 wherein said collecting means is fixed to said fluid communication means by a suture.

26. The endoscopic component of claim 24 wherein said collecting means is fixed to said fluid communication means by a weld.

27. The endoscopic component of claim 15 being adapted to be received in a tubular element and being movable through said tubular element.

28. The endoscopic component of claim 27 wherein said tubular element is a silicone sleeve.

29. The endoscopic wound care component of claim 15, wherein the collecting means is integrally formed with the fluid communication means.

30. The endoscopic wound care component of claim 15, wherein the collecting means is fixedly connected to the fluid communication means by a non-absorbable surgical suture, a bio-absorbable suture, or welding.

\* \* \* \* \*